United States Patent
Nakao et al.

(10) Patent No.: US 7,572,630 B2
(45) Date of Patent: Aug. 11, 2009

(54) METHOD FOR DIFFERENTIATING PRIMATE EMBRYONIC STEM CELL INTO VASCULAR CELL

(75) Inventors: Kazuwa Nakao, Kyoto (JP); Hiroshi Itoh, Kyoto (JP); Jun Yamashita, Kyoto (JP); Masakatsu Sone, Osaka (JP); Yasushi Kondo, Osaka (JP); Yutaka Suzuki, Osaka (JP)

(73) Assignee: Mitsubishi Tanabe Pharma Corporation, Osaka-Shi (JP)

( * ) Notice: Subject to any disclaimer, the term of this patent is extended or adjusted under 35 U.S.C. 154(b) by 476 days.

(21) Appl. No.: 11/063,584

(22) Filed: Feb. 24, 2005

(65) Prior Publication Data

US 2005/0191744 A1 Sep. 1, 2005

Related U.S. Application Data

(60) Provisional application No. 60/547,809, filed on Feb. 27, 2004.

(51) Int. Cl.
*C12N 5/00* (2006.01)
*C12N 5/06* (2006.01)
*C12N 5/10* (2006.01)

(52) U.S. Cl. .................... 435/325; 435/347; 435/363; 435/373; 435/374; 435/375

(58) Field of Classification Search .................. None
See application file for complete search history.

(56) References Cited

OTHER PUBLICATIONS

Hoffman et al, Nature Biotechnology 23:699-708, 2005.*
Sone et al, Arterioscler Thromb Vasc Biol. Oct. 2007;27(10):2127-34.*
Oyamada et al, J Transl Med. Sep. 30, 2008;6:54.*
Yamahara et al, PLoS ONE. Feb. 27, 2008;3(2):e1666.*
Nature, vol. 408, Nov. 2, 2000, pp. 92-96.
Blood, vol. 101, No. 7, Apr. 1, 2003, pp. 2675-2678.
Circulation, Apr. 29, 2003, Sone et al., pp. 2085-2088.
Nature, vol. 408, Nov. 2, 2000, pp. 92-96, Yamashita et al.
Blood, vol. 101, No. 7, Apr. 1, 2003, pp. 2675-2678, Yurugi-Kobyashi et.

* cited by examiner

*Primary Examiner*—Sumesh Kaushal
(74) *Attorney, Agent, or Firm*—Birch, Stewart, Kolasch & Birch, LLP

(57) ABSTRACT

To provide a technique of the differentiation from a primate embryonic stem cell into a vascular cell, and techniques using the same. A method for differentiating a primate embryonic stem cell into a vascular cell, comprising differentiating a primate embryonic stem cell into a VEGFR-2-positive and undifferentiated primate embryonic stem cell marker-negative cell, and if need, further differentiating the resulting cell, a method of the differentiation into a vascular cell, and a vascular cell obtained by the method.

12 Claims, 4 Drawing Sheets

METHOD FOR DIFFERENTIATING PRIMATE EMBRYONIC STEM CELL INTO VASCULAR CELL

CROSS-REFERENCE TO RELATED APPLICATION

The present application claims the benefit of U.S. Provisional Application No. 60/547,809, filed on Feb. 27, 2004, the subject matter of which is hereby incorporated herein by reference.

BACKGROUND OF THE INVENTION

1. Field of the Invention

The present invention relates to a method for differentiating a primate embryonic stem cell into a vascular cell. More particularly, the present invention relates to a differentiation method comprising differentiating a primate embryonic stem cell into a vascular cell, and obtaining the vascular cell; the vascular cell; and a method for producing the vascular cell.

2. Description of the Related Art

Recently, studies on the differentiation and regeneration of various organs have been advanced, and the regenerative therapies in the field of clinical medicine have been brought into view as actual subjects of studies. Therefore, it has been placed more expectations on regenerative medicine day by day. Inter alias, a study using an embryonic stem cell having an ability to differentiate into all types of cells or organs in a living body is one of main themes in clarification of the mechanism of development or differentiation and regenerative medicine.

So far, studies on a mouse embryonic stem cell have been progressed. In addition, an embryonic stem cell of a primate such as a human and a monkey has been established. It has been revealed that a primate embryonic stem cell greatly differs from a mouse embryonic stem cell in, for example, a form of a colony, expression manners of cell surface antigens, a proliferation and division rate, and dependency on leukemia inhibitory factor (LIF) [Pera et al., Journal of Cell Science, 113, 5-10 (2000)].

On the other hand, in the regenerative therapy for vascular vessel, for example, a clinical trial regarding a vascular regenerative medicine using a single angiogenesis factor such as vascular endothelial growth factor, basic fibroblast growth factor, hepatic growth factor or the like has been performed on ischemic diseases. However, as described above, the vascular regenerative medicine using angiogenesis factor has a defect that the vascular regenerative medicine has disadvantages in safety, since in a random double blind control clinical trial using bFGF in a coronary disease, a symptom is improved by the vascular regenerative medicine in a short term but not in a long term. Therefore, under current situation, it is desired that in vascular regenerative therapy, a correct vascular structure composed of an endothelial cell tube having a mural cell is generated.

SUMMARY OF THE INVENTION

The present invention relates to a technique of the differentiation from a primate embryonic stem cell into a vascular cell, and techniques using the same.

In one aspect, the present invention relates to providing a method for differentiating a primate embryonic stem cell into a vascular cell, which allows to achieve at least any one of a supply of a vascular cell capable of achieving at least any one of long-term culture, subculture, in vitro proliferation, a graft survival at a high efficiency, obtaining of high compatibility, and efficient angiogenesis (e.g., vascularization and the like); a supply of the vascular cell in a large amount; a supply of a material for treating a vascular disease (e.g., ischemic diseases and the like); and an induction of a cell population at each stage of angiogenesis differentiation, and clarification of characteristics thereof.

In addition, in another aspect, the present invention relates to providing a method for producing a vascular cell, which enables to achieve at least any one of a supply of a vascular cell capable of achieving at least any one of long-term culture, subculture, in vitro proliferation, a graft survival at a high efficiency, obtaining of high compatibility, and efficient angiogenesis (e.g., vascularization and the like); a supply of the vascular cell in a large amount; a supply of a material for treating a vascular disease (e.g., ischemic diseases and the like); and an exhaustive analysis of gene expression of a cell population at each stage of angiogenesis differentiation, and identification of novel factors involved in angiogenesis differentiation.

Also, in still another aspect, the present invention relates to providing a vascular cell, specifically, a vascular progenitor cell, a vascular endothelial cell, a mural cell and a vascular construct, which enables to achieve at least any one of long-term culture, subculture, in vitro proliferation, a graft survival at a high efficiency, obtaining high compatibility, and efficient angiogenesis (e.g., vascularization and the like).

Specifically, the gist of the present invention is:

[1] a method for differentiating a primate embryonic stem cell into a vascular cell, comprising differentiating a primate embryonic stem cell into a vascular endothelial growth factor receptor (VEGFR-2)-positive and undifferentiated primate embryonic stem cell marker-negative cell;

[2] the differentiation method according to the above item [1], comprising the steps of:
(I) co-culturing a primate embryonic stem cell with a feeder cell, to differentiate into a cell population A comprising a vascular endothelial growth factor receptor (VEGFR-2)-positive and undifferentiated primate stem cell marker-negative cell, and
(II) separating substantially the VEGFR-2-positive and undifferentiated primate embryonic stem cell marker-negative cell from the cell population A obtained in the above step (I);

[3] the differentiation method according to the above item [1] or [2], wherein the vascular cell is a vascular progenitor cell;

[4] a method for differentiating a primate embryonic stem cell into a vascular cell, comprising differentiating a primate embryonic stem cell into a vascular endothelial growth factor receptor (VEGFR-2)-positive and undifferentiated primate embryonic stem cell marker-negative cell, and further differentiating the resulting cell;

[5] the differentiation method according to the above item [4], comprising the steps of:
(I) co-culturing a primate embryonic stem cell with a feeder cell, to differentiate into a cell population A comprising a vascular endothelial growth factor receptor (VEGFR-2)-positive and undifferentiated primate embryonic stem cell marker-negative cell,
(II) separating substantially the VEGFR-2-positive and undifferentiated primate embryonic stem cell marker-negative cell from the cell population A obtained in the above step (I),
(III) culturing the VEGFR-2-positive and undifferentiated primate embryonic stem cell marker-negative cell obtained in the above step (II) in the presence of serum or PDGF- BB, to differentiate into a cell population B comprising a mural cell marker-positive cell, and (IV) separating substantially the mural cell marker-positive cell from the cell population B obtained in the above step (III);

[6] the differentiation method according to the above item [4], comprising the steps of:

(I) co-culturing a primate embryonic stem cell with a feeder cell, to differentiate into a cell population A comprising a vascular endothelial growth factor receptor (VEGFR-2)-positive and undifferentiated primate embryonic stem cell marker-negative cell, (II) separating substantially the VEGFR-2-positive and undifferentiated primate embryonic stem cell marker-negative cell from the cell population A obtained in the above step (I), (III') culturing the VEGFR-2-positive and undifferentiated primate embryonic stem cell marker-negative cell obtained in the above step (II) in the presence of VEGF, to differentiate into a cell population C comprising a vascular endothelial cell marker-positive cell, and (IV') separating substantially the vascular endothelial cell marker-positive cell from the cell population C obtained in the above step (III');

[7] the differentiation method according to the above item [4], comprising the steps of:

(I) co-culturing a primate embryonic stem cell with a feeder cell, to differentiate into a cell population A comprising a vascular endothelial growth factor receptor (VEGFR-2)-positive and undifferentiated primate embryonic stem cell marker-negative cell, (II) separating substantially the VEGFR-2-positive and undifferentiated primate embryonic stem cell marker-negative cell from the cell population A obtained in the above step (I), and (III") culturing three-dimensionally the VEGFR-2-positive and undifferentiated primate embryonic stem cell marker-negative cell obtained in the above step (II) in the presence of VEGF and phorbol 12-myristate 13-acetate within a carrier;

[8] a method for producing a vascular cell, comprising the steps of:

(I) co-culturing a primate embryonic stem cell with a feeder cell, to differentiate into a cell population A comprising a vascular endothelial growth factor receptor (VEGFR-2)-positive and undifferentiated primate embryonic stem cell marker-negative cell, and (II) separating substantially the VEGFR-2-positive and undifferentiated primate embryonic stem cell marker-negative cell from the cell population A obtained in the above step (I);

[9] a method for producing a vascular cell, comprising the steps of:

(I) co-culturing a primate embryonic stem cell with a feeder cell, to differentiate into a cell population A comprising a vascular endothelial growth factor receptor (VEGFR-2)-positive and undifferentiated primate embryonic stem cell marker-negative cell, (II) separating substantially the VEGFR-2-positive and undifferentiated primate embryonic stem cell marker-negative cell from the cell population A obtained in the above step (I), (III) culturing the VEGFR-2-positive and undifferentiated primate embryonic stem cell marker-negative cell obtained in the above step (II) in the presence of serum or PDGF-BB, to differentiate into a cell population B comprising a mural cell marker-positive cell, and (IV) separating substantially the mural cell marker-positive cell from the cell population B obtained in the above step (III);

[10] a method for producing a vascular cell, comprising the steps of:

(I) co-culturing a primate embryonic stem cell with a feeder cell, to differentiate into a cell population A comprising a vascular endothelial growth factor receptor (VEGFR-2)-positive and undifferentiated primate embryonic stem cell marker-negative cell, (II) separating substantially the VEGFR-2-positive and undifferentiated primate embryonic stem cell marker-negative cell from the cell population A obtained in the above step (I), (III') culturing the VEGFR-2-positive and undifferentiated primate embryonic stem cell marker-negative cell obtained in the above step (II) in the presence of VEGF, to differentiate into a cell population C comprising a vascular endothelial cell marker-positive cell, and (IV') separating substantially the vascular endothelial cell marker-positive cell from the cell population C obtained in the above step (III');

[11] a method for producing a vascular cell, comprising the steps of:

(I) co-culturing a primate embryonic stem cell with a feeder cell, to differentiate into a cell population A comprising a vascular endothelial growth factor receptor (VEGFR-2)-positive and undifferentiated primate embryonic stem cell marker-negative cell, (II) separating substantially the VEGFR-2-positive and undifferentiated primate embryonic stem cell marker-negative cell from the cell population A obtained in the above step (I), and (III") culturing three-dimensionally the VEGFR-2-positive and undifferentiated primate embryonic stem cell marker-negative cell obtained in the above step (II) in the presence of VEGF and phorbol 12-myristate 13-acetate within a carrier;

[12] a vascular cell obtained by the method of the above item [8], wherein the vascular endothelial growth factor receptor (VEGFR-2)-positive and undifferentiated primate embryonic stem cell marker-negative cell is a vascular progenitor cell;

[13] a vascular cell obtained by the method of the above item [9], wherein the mural cell marker-positive cell is a mural cell;

[14] a vascular cell obtained by the method of the above item [10], wherein the vascular endothelial cell marker-positive cell is a vascular endothelial cell; and

[15] a vascular cell obtained by the method of the above item [11], wherein the vascular cell is a vascular construct.

DETAILED DESCRIPTION OF THE INVENTION

Figure 1:
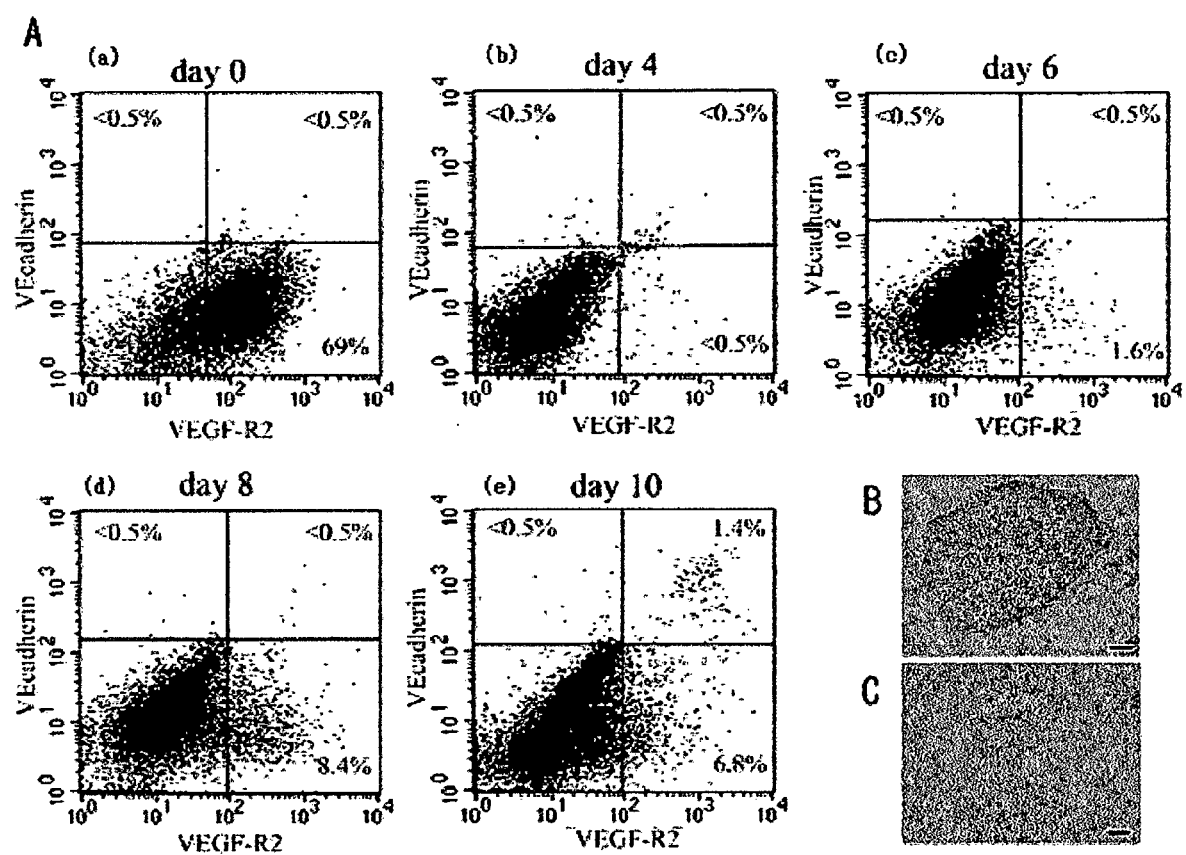
FIG. 1 is a view showing the results of the studies on the properties of cells obtained by the differentiation of a monkey embryonic stem cell. Panel A shows the results of analysis of cells (results of flow cytometry analysis), and (a), (b), (c), (d) and (e) show cells obtained on days 0, 4, 6, 8 and 10, respectively. Panel B shows the results of investigation of the presence or absence of alkaline phosphatase activity in an undifferentiated embryonic stem cell. Panel C shows the results of investigation of the presence or absence of alkaline phosphatase activity in an embryonic stem cell-derived cell population on day 8.

One aspect of the present invention is a method for differentiating a primate embryonic stem cell into a vascular cell, comprising differentiating a primate embryonic stem cell into a vascular endothelial growth factor receptor (VEGFR-2)-positive and undifferentiated primate embryonic stem cell marker-negative cell.

In the present specification, the term "vascular cell" means the concept including a vascular progenitor cell, a vascular endothelial cell and a vascular mural cell, unless otherwise indicated.

According to the differentiation method of the present invention, since a primate embryonic stem cell, in particular, a human embryonic stem cell, which can indefinitely proliferate by self-renewalty, is used, a vascular structural material leading to clinical application in the regenerative medicine field can be supplied in a large amount and effectively.

In addition, according to the differentiation method of the present invention, since a primate embryonic stem cell which can be cultured for a long term and can be subcultured is used, a vascular cell which can be proliferated in vitro, for example, a vascular progenitor cell can be obtained.

Further, according to the differentiation method of the present invention, since a primate embryonic stem cell is used, there can be obtained a vascular cell which can be grafted in a living body of a primate, for example, a human and a monkey, preferably, s human, at a high efficiency and can have high compatibility.

The above VEGFR-2-positive and undifferentiated primate embryonic stem cell marker-negative cell is a vascular cell capable of exhibiting performances as a vascular progenitor cell in a primate.

In addition, another aspect of the present invention is a method for differentiating a primate embryonic stem cell into a vascular cell, comprising differentiating a primate embryonic stem cell into a vascular endothelial growth factor receptor (VEGFR-2)-positive and undifferentiated primate embryonic stem cell marker-negative cell, and additionally differentiating the resulting cell.

In a mouse, the differentiation into a vascular cell can be induced by using a cell with VEGFR-2-positive which is an index of a vascular progenitor cell. However, in a primate, unexpectedly, even undifferentiated embryonic stem cell expressed VEGFR-2, and the differentiation into a vascular cell such as a vascular endothelial cell and a mural cell could not be induced even when a VEGFR-2-positive cell was used. However, in the differentiation method of the present invention, by additionally differentiating VEGFR-2-positive and undifferentiated primate embryonic stem cell marker-negative cell which was induced from embryonic stem cell, there are exhibited excellent effects such that a vascular cell is obtained with a high precision and efficiently.

One embodiment of the differentiation method of the present invention includes, specifically, a method (differentiation method 1) comprising the steps of:

(I) co-culturing a primate embryonic stem cell with a feeder cell to differentiate into a cell population A comprising a VEGFR-2-positive and undifferentiated primate embryonic stem cell marker-negative cell, and (II) separating substantially the VEGFR-2-positive and undifferentiated primate embryonic stem cell marker-negative cell from the cell population A obtained in the above step (I).

In the present specification, the "primate" refers to a human, a monkey and the like. The above monkey includes, for example, a crab-eating macaque, a rhesus monkey, a Japanese monkey, a marmoset and the like.

In the present specification, the "primate embryonic stem cell" refers to an undifferentiated cell having both pluripotency and self-renewality, more specifically, refers to a cell exhibiting properties of alkaline phosphatase (ALP) activity-positive, SSEA-3-positive, SSEA-4-positive, TRA1-60-positive and TRA1-81-positive. The properties can be confirmed by a method such as immunostaining with the conventional antibody such as anti-SSEA-1 antibody, anti-SSEA-3 antibody, anti-SSEA-4 antibody, anti-TRA1-60 antibody and anti-TRA1-81 antibody, or alkaline phosphatase activity measuring means [e.g., commercially available ALP detection kit (manufactured by SIGMA)].

The above immunostaining can be performed by the conventional procedures [see, for example, Hirashima et al., *Blood*, 93, 1253-1263 (1999), all teachings of which are incorporated herein by reference].

In the present specification, the "undifferentiated primate embryonic stem cell marker" includes, for example, ALP, SSEA-3, SSEA-4, TRA1-60, TRA1-81 and the like.

The primate embryonic stem cell used in the above step (I) includes, for example, CMK-6 cell strain, HES-3 cell strain and the like. The undifferentiated state of the primate embryonic stem cell can be maintained, for example, according to Hirofumi Suemori et al. [*Dev. Dynamics*, 222, 273-279 (2001), all teachings of which are incorporated herein by reference], Benjamin E. Reubinof et al. [*Nature Biotech.*, 18, 399-404 (2000), all teachings of which are incorporated herein by reference] or the like.

The primate embryonic stem cell used in the above step (I) can be maintained and proliferated by culturing in a medium for an embryonic stem cell using appropriate feeder cells.

As the feeder cell used for maintaining the undifferentiated state of an embryonic stem cell and proliferating the embryonic stem cell, a cell which is conventionally used in culturing an embryonic stem cell may be used. For example, the feeder cell includes cells obtained by subjecting a mouse fetus-derived fibroblast strain, a mouse marrow cell strain defective in macrophage stimulating factor, a mouse yolk sac cell strain defective in macrophage stimulating factor and the like to mitomycin C treatment or X-ray treatment. The mouse marrow cell strain includes, for example, S17 cell strain [Collins et al., *J. Immunol.*, published in 1987, vol. 138, p 1082-1087, all teachings of which are incorporated herein by reference]. The mouse yolk sac cell strain includes, for example, C166 cell strain [Wang et al., *In Vitro Cell. Dev. Biol. Anim.*, published in 1996, vol. 32, p 292-299, all teachings of which are incorporated herein by reference].

In addition, the feeder cell used for maintaining the undifferentiated state of an embryonic stem cell and proliferating the embryonic stem cell is varied depending on a kind of the cell. For example, when a mouse fetus-derived fibroblast is used as a feeder cell, a feeder layer can be obtained by culturing the mouse fetus-derived fibroblast to confluent on a 10 cm dish coated with a 0.1% by weight aqueous gelatin solution [derived from cow skin, manufactured by SIGMA], and subjecting the fibroblast to mitomycin C treatment or X-ray irradiation.

Culturing condition for the feeder cell is varied depending on a kind of the cell. The conditions include, for example, maintenance at 36 to 38° C., preferably 37° C. in a vapor phase of 5% $CO_2$.

In addition, as a medium used for maintaining the undifferentiated state of and proliferating an embryonic stem cell, for example, conventional culture medium ingredients depending on an animal species which is a source for supplying an embryonic stem cell to be used may be used, being not limited. Culture medium ingredients are varied depending on a subject embryonic stem cell. The culture medium ingredients, include for example, Dulbecco's modified Eagle medium/F12 medium containing β-mercaptoethanol, a non-essential amino acid and serum or a serum substitute (e.g., 20% by weight KNOCKOUT-™ Serum Replacement) [manufactured by Invitrogen] and the like, when used in a monkey embryonic stem cell or a human embryonic stem cell.

Further, when used in a human embryonic stem cell, the culture medium ingredients includes Dulbecco's modified Eagle medium containing, as components, β-mercaptoethanol, a non-essential amino acid and serum or a serum substitute (e.g., 20% by weight KNOCKOUT-™ Serum Replacement manufactured by Invitrogen).

Culturing conditions for maintaining the undifferentiated state of and proliferating the primate embryonic stem cell are varied depending on a kind of an embryonic stem cell. The culturing conditions include, for example, maintenance at 36 to 38° C., more preferably 37° C., preferably, in a vapor phase of 5% by volume of $CO_2$ in the case of a monkey embryonic stem cell or a human embryonic stem cell.

In the case of a monkey embryonic stem cell, the primate embryonic stem cell used in the above step (I) is desirably a cell which has been treated by an appropriate means, for example, a reagent suitable for dissociating cells [e.g., trade name: Dissociation Buffer (manufactured by GIBCO), collagenase, dispase, trypsin and the like] and dissociated. In addition, in the primate embryonic stem cell, in the case where the growth rate is remarkably reduced when the cells are separated into single cells, a small cluster of cells obtained by treatment with a proper means, for example, a reagent suitable for dissociating cells [e.g., collagenase, dispase and the like] may be substituted.

From the viewpoint of possession of ability to differentiate into a vascular cell such as a vascular progenitor cell and obtainment of graft survival of a cell, the feeder cell used in the above step (I) may be a cell capable of promoting the differentiation from an embryonic stem cell into a vascular or hemocyte cell and expressing various physiologically active substances or adhesion factors. The feeder cell includes a stroma cell such as a calvaria fibroblast. Specifically, the feeder cell includes OP9 cell strain.

In the above step (I), co-culture of a primate embryonic stem cell and a feeder cell is performed by plating a primate embryonic stem cell on the feeder layer, and culturing the cell under the conditions suitable for the differentiation. In the above step (I), it is desirable that the amount of a primate embryonic stem cell to be plated on the feeder layer is, for example, preferably $2 \times 10^4$ cells to $5 \times 10^5$ cells per 10 cm diameter cell tissue culture dish, in the case of a monkey embryonic stem cell. When a cell small mass is plated, it is difficult to precisely grasp the number of cells, but the cell small mass may be plated at the same cell density as in the usual subculture of an embryonic stem cell.

In addition, the conditions suitable for the differentiation are varied depending on a kind of an embryonic stem cell. For example, in the case of a monkey embryonic stem cell or a human embryonic stem cell, the conditions include maintenance at 36 to 38° C., more preferably 37° C., preferably for 8 to 10 days, more preferably for 8 days, preferably in a vapor of 5% by volume of $CO_2$.

As a medium used in co-culture, a medium suitable for differentiating the embryonic stem cell may be used depending on the kind of an embryonic stem cell. Specifically, the medium includes, for example, a differentiation culture medium [composition: αMEM culture medium containing $5 \times 10^{-5}$ M 2-mercaptoethanol and 10% by weight of serum].

As a culturing container used for co-culture, a container suitable for cell culture may be used. The container includes a tissue culture dish having a diameter of 6 cm or 10 cm.

In the above step (I), when serum is used in a medium, it is desirable that the concentration of the serum is preferably 10% by weight.

In the above step (I), a cell population A comprising a VEGFR-2-positive and undifferentiated primate embryonic stem cell marker-negative cell can be obtained by removing a culture supernatant from a culture obtained by co-culture, washing the culturing container with a suitable solution which does not affect on a cell, for example, phosphate buffered physiological saline, Hanks' Balanced Salt Solution (HBSS), physiological saline or serum-free medium such as RPMI-1640, and then treating the culturing container after washing with a reagent suitable for dissociating cells [e.g., trade name: Dissociation Buffer (manufactured by GIBCO), collagenase, dispase, trypsin solution and the like].

In the cell population A obtained in the above step (I), the desired differentiated cell, namely, "VEGFR-2-positive and undifferentiated embryonic stem cell marker-negative cell" can be confirmed, for example, by immunostaining with anti-VEGFR antibody and anti-TRA1-60 antibody, the conventional alkaline phosphatase activity measuring means [commercially available ALP detection kit (manufactured by Sigma)] or the like.

In addition, an antibody used in the present invention may be any of a commercially available antibody, an antibody prepared by the conventional procedure and an antibody fragment thereof.

Then, in the above step (II), the "VEGFR-2-positive and undifferentiated embryonic stem cell marker-negative cell" is separated from the cell population A.

In the above step (II), the separation of the desired cell, namely, the separation of the "VEGFR-2-positive and undifferentiated embryonic stem cell marker-negative cell" can be performed by an appropriate cell sorting means, for example, cell sorting by conventional flow cytometry [FACS (Fluorescence Activated Cell Sorter)] or cell sorting by MACS (Magnetic Activated Cell Sorter). In the FACS, the desired cell may be sorted using as an index a label of a labeled antibody suitable for sorting. In addition, in the MACS, the desired cell may be sorted by binding magnetic beads retaining an antibody suitable for sorting with an target cell, and recovering magnetic beads.

In the above step (II), as the antibody, for example, anti-VEGFR-2 antibody, anti-VE cadherin antibody, anti-TRA1-60 antibody and the like can be used.

For example, when flow cytometry is used, the desired cell can be isolated by suspending the cell population in an appropriate solution, to obtain a cell suspension having an appropriate cell concentration, and subjecting the resulting cell suspension to flow cytometry to perform cell sorting.

The "suitable solution" used for suspending the cell may be a solution suitable for performing flow cymerty and cell sorting. The suitable solution includes a phosphate buffered physiological saline (PBS), Hanks' Balanced Salt Solution (HBSS) and the like.

In addition, the cell concentration in the above cell suspension may be a concentration at which a plurality of cells can be sufficiently discriminated electrically upon flow cytometry and cell sorting, and can be appropriately set depending on the cell sorting instrument to be used. For example, it is desirable that the concentration is preferably $1 \times 10^6$ cells/ml to $1 \times 10^7$ cells/ml.

Conditions for flow cytometry and cell sorting can be appropriately set depending on the sorting manner (e.g., water droplet charging manner, cell capturing manner) in flow cytometry to be used.

The above conditions may be the number of sorting droplets, the number of cells to be sorted and the flow rate, which are suitable for obtaining the desired cell at a high purity.

When the separation is performed by FACS, a labeling substance used in a labeled antibody includes a fluorescent dye. The substance can be appropriately selected depending on a kind of laser light and a filter of flow cytometer used. The substance includes, for example, fluorescein isothiocyanate (FITC), phycoerythrin (PE), allophycocyanin (APC), Texas Red (TR), Cy3, Cy5, PerCO (trade mark) [manufactured by BD Biosciences], Red613 (trade mark) [manufactured by GIBCO], Red670 (trade mark) [manufactured by GIBCO], Alexa647 (manufactured by Molecular Sieves), Alexa488 (manufactured by Molecular Sieves) and the like.

The cell separated in the above step (II) can be evaluated by immunostaining with an antibody which is different from the antibody used in sorting.

Another embodiment of the differentiation method of the present invention includes, specifically a method further comprising, in addition to the above steps (I) and (II), (III) culturing the "VEGFR-2-positive and undifferentiated embryonic stem cell marker-negative cell" obtained in the above step (II) in the presence of serum or PDGF-BB to differentiate into a cell population B comprising a mural cell marker-positive cell, and (IV) separating substantially the mural cell marker-positive cell from the cell population B obtained in the above step (III), (differentiation method 2).

In the above step (III), in culture in the presence of serum or PDGF-BB, for example, the above differentiation culture medium [composition: αMEM culture medium containing $5 \times 10^{-5}$M 2-mercaptoethanol and 10% by weight of serum] or a medium containing 10 ng/ml PDGF-BB in place of serum in the above differentiation culture medium can be used. The concentration of serum or PDGF-BB in the above differentiation culture medium may be appropriately changed in a range of 1 to 20 ng/ml.

In the specification, the "mural cell marker" includes, for example, a smooth muscle actin (αSMA), calponin and the like.

In culturing in the presence of serum or PDGF-BB in the above step (III), the cell obtained in the (II) is plated on an appropriate culturing container coated with type IV collagen or the other extracellular matrices, for example, a 24-well dish, and culturing may be performed using a differentiation culture medium under the same conditions as conditions suitable for the above differentiation.

It is desirable that the culturing time period is preferably 5 to 10 days, more preferably 6 to 8 days from the viewpoint of appropriate differentiation.

In the cell population B obtained in the above step (III), the desired differentiated cell, that is, the mural cell marker-positive cell can be confirmed by immunostaining with an anti-mural cell marker antibody.

Then, in the above step (IV), the mural cell marker-positive cell is substantially separated from the cell population B obtained in the above step (III).

In the above step (IV), the separation of the mural cell marker-positive cell can be performed using an anti-mural cell marker antibody in the same manner as in the above step (II).

In the present specification, the "anti-mural cell marker antibody" includes, for example, anti-αSMA antibody, anti-calponin antibody and the like.

The cell separated in the above step (IV) can be evaluated by immunostaining with an antibody which is different from the antibody used for sorting.

Another embodiment of the differentiation method of the present invention includes, specifically, a method further comprising, after the above steps (I) and (II) are performed, (III') culturing the "VEGFR-2-positive and undifferentiated embryonic stem cell marker-negative cell" obtained in the above step (II) in the presence of VEGF to differentiate into a cell population C comprising a vascular endothelial cell marker-positive cell, and (IV') separating substantially the vascular endothelial cell marker-positive cell from the cell population C obtained in the above step (III')

(differentiation method 3).

In the present specification, the "vascular endothelial cell marker" includes, for example, CD34, VE cadherin, PECAM1, eNOS and the like.

In culture in the presence of VEGF in the above step (III'), for example, the above differentiation culture medium [composition: αMEM culture medium containing $5 \times 10^{-5}$M 2-mercaptoethanol, 10% by weight of serum and 50 ng/ml VEGF] can be used. The concentration of each of serum and VEGF in the differentiation culture medium may be appropriately changed in a range of 2% by weight to 10% by weight for serum, and 10 to 100 ng/ml of VEGF.

In the above step (III'), the cell obtained in the (II) may be plated on an appropriate culturing container, for example, a 24-well dish, coated with type IV collagen, other extracellular matrices or the like, and culturing may be performed using a differentiation culture medium under the same conditions as the above conditions suitable for the differentiation.

In addition, from the viewpoint of appropriate differentiation, it is desirable that the culture time period is preferably 5 to 10 days, more preferably 6 to 8 days.

Then, in the above step (IV'), a vascular endothelial cell marker-positive cell is substantially separated from the cell population C obtained in the above step (III').

In the above step (IV'), the separation of a vascular endothelial cell marker-positive cell can be performed using an anti-vascular endothelial cell marker antibody and the like, in the same manner as in the above step (II).

In the present specification, the "anti-vascular endothelial cell marker antibody" includes, for example, anti-CD 34 antibody, anti-VE cadherin antibody, anti-PECAM1 antibody, anti-eNOS antibody and the like.

The cell separated in the above step (IV') can be evaluated by immunostaining with an antibody which is different from the antibody used in sorting.

Another embodiment of the differentiation method of the present invention includes, specifically, a method comprising, in addition to the above steps (I) and (II), (III") culturing three-dimensionally the "VEGFR-2-positive and undifferentiated embryonic stem cell marker-negative cell" obtained in the above step (II) in the presence of VEGF and phorbol 12-myristate 13-acetate within a carrier (differentiation method 4).

In the above step (III"), three-dimensional culture is not particularly limited, and for example, can be performed by embedding the "VEGFR-2-positive and undifferentiated embryonic stem cell marker-negative cell" within a carrier, or making a carrier to carry the cell, and culturing the cell using a medium suitable for the differentiation in the presence of VEGF and phorbol 12-myristate 13-acetate under conditions suitable for the differentiation; or by making a cell mass of VEGFR-2-positive and undifferentiated embryonic stem cell marker-negative cells by a hanging drop method, embedding the cell mass within a carrier, and culturing three-dimensionally the mass.

The carrier may be any carrier as long as it exhibits properties of a gel-like structure composed of an extracellular matrix. The carrier includes, for example, a collagen gel, MATRIGEL and the like. Among them, a collagen IA gel is desirable.

From the viewpoint of formation of a structure of a vascular cell, it is desirable that the number of cells to be used in three-dimensional culture is a cell mass of $1 \times 10^2$ to $10^3$ cells.

The above "medium suitable for the differentiation", but not being particularly limited thereto, includes, for example, αMEM culture medium containing $5 \times 10^{-5}$M 2-mercaptoethanol and 10% by weight of serum.

From the viewpoint of the differentiation of a vascular endothelial cell, it is desirable that a concentration of VEGF in the medium is 10 ng/ml to 100 ng/ml, preferably 50 ng/ml to 100 ng/ml, more preferably 50 ng/ml.

From the viewpoint of formation of an appropriate tubular structure, it is desirable that a concentration of phorbol 12-myristate 13-acetate in the medium is 10 μM to 100 μM, more preferably 100 μM.

The above step (III") is not particularly limited, and can be specifically performed by, for example, embedding the cell population A within a collagen gel (2.0 mg/ml) (trade name: Cellmatrix type 1-A manufactured by Nitta Gelatin Inc.), placing the resulting product on a trade name: Cell Disk (manufactured by Sumitomo Bakelite Co., Ltd.), placing the Cell Disk in a well of a 24-well dish [manufactured by BD Biosciences], and culturing three-dimensionally the resultant in a differentiation culture medium [composition: αMEM culture medium containing $5 \times 10^{-5}$M 2-mecaptoethanol and 10% by weight of serum (manufactured by GIBCO)] containing 50 ng/ml of VEGF and 100 nM of phorbol 12-myristate 13-acetate [manufactured by SIGMA].

The cell obtained by performing the differentiation method 1 is a cell having properties as a vascular progenitor cell of a primate (hereinafter, vascular progenitor cell). The cell obtained by performing the differentiation method 2 is a cell having properties as a mural cell of a primate (hereinafter, mural cell). Further, the cell obtained by performing the differentiation method 3 is a cell having properties as a vascular endothelial cell of a primate (hereinafter, vascular endothelial cell). In addition, the cell obtained by performing the differentiation method 4 is a construct showing a vascular structure of a primate (hereinafter, vascular construct).

Accordingly, in another aspect of the present invention, there are also provided a vascular cell of a primate, specifically, a vascular progenitor cell, a mural cell, a vascular endothelial cell and a vascular construct, as well as a method for producing a vascular cell of a primate.

In the method for producing a vascular cell of the present invention, since steps based on the differentiation method of the present invention are performed, and since a primate embryonic stem cell which can indefinitely proliferate by self-renewality, in particular, a human embryonic stem cell is used, a vascular construction material leading to clinical application in the regeneration medical field can be produced in a large amount and effectively.

In addition, in the method for producing a vascular cell of the present invention, steps based on the differentiation method of the present invention are performed. Therefore, there can be achieved in vitro proliferation, graft survival on a primate, for example, a human and a monkey, preferably, on a human living body in a high efficiency, and high compatibility.

In addition, according to the process of the present invention, a vascular cell can be supplied in a large amount.

The production method of the present invention can be performed by the same steps as those of the differentiation method of the present invention. Specifically, examples include:

a method for producing a vascular cell, specifically, a vascular progenitor cell, comprising the above step (I) and the above step (II) (production method 1);

a method for producing a vascular cell, specifically, a mural cell, comprising the above step (I), the above step (II), the above step (III) and the above step (IV) (production method 2);

a method for producing a vascular cell, specifically, a vascular endothelial cell, comprising the above step (I), the above step (II), the above step (III') and the above step (IV') (production method 3); and a method for producing a vascular cell, specifically, a vascular construct, comprising the above step (I), the above step (II), and the above step (III') (production method 4).

Specifically, the vascular cell obtained by the production method of the present invention includes:

a vascular progenitor cell obtained by the production method 1, which is vascular endothelial growth factor receptor (VEGFR-2)-positive and undifferentiated embryonic stem cell marker-negative;

a mural cell obtained by the production method 2, which is mural cell marker-positive;

a vascular endothelial cell obtained by the production method 3, which is vascular endothelial cell marker-positive; and a vascular construct obtained by the production method 4.

Since the vascular cell of the present invention is produced by the method of the present invention, there are exhibited excellent properties such that the vascular cell can be proliferated in vitro.

The present invention will be explained in detail below by Examples, but the present invention is not limited to the Examples at all.

EXAMPLE 1

Differentiation from Monkey Embryonic Stem Cell

As a monkey embryonic stem cell, a crab-eating macaque embryonic stem cell, CMK-6 cell strain [Hirofumi Suemori et al., *Developmental Dynamics*, 222,273-279 (2001), all teachings of which are incorporated herein by reference] was used.

A cell dissociation buffer [manufactured by GIBCO] was added to monkey embryonic stem cells maintained on a dish containing an undifferentiation maintaining medium [composition per 200 ml: 163 ml of Dulbecco's modified minimum essential medium (DMEM)/F12, 30 ml of bovine fatal serum (final concentration of 15% by weight), 2 ml of L-glutamine (final concentration of 2 mM), 2 ml of penicillin (100 U/ml)-streptomycin (100 μg/ml), 2 ml of non-essential amino acid solution, 1 ml of 2-mercaptoethanol (final concentration of 0.1 mM)]. The monkey embryonic stem cells were incubated at 37° C. for 10 minutes. Thereafter, the embryonic stem cells were recovered by tapping the dish and then detaching the cells in the single cell state from the dish by pippeting.

OP9 cell strain was cultured to be confluent on a 10-cm dish coated with 0.1% by weight of an aqueous gelatin solution [derived from cow skin, manufactured by SIGMA] to obtain an OP9 feeder layer.

The recovered embryonic stem cells ($5 \times 10^4$ cells) were plated on the OP9 cell strain. Thereafter, 20 ml of a differentiation culture medium [composition: αMEM culture medium containing $5 \times 10^{-5}$ M 2-mercaptoethanol and 10% by weight of serum (manufactured by GIBCO)] was added to the cell. The embryonic stem cell was co-cultured with OP9 cell at 37° C. in 5% by volume of $CO_2$ for 8 days.

The culture supernatant was removed from the resulting culture, and the dish was washed with a phosphate-buffered physiological saline. Then, 2 ml of the cell dissociation buffer was added to the dish after washing. The cells were incubated at 37° C. for 10 minutes. As a result, the OP9 cell remained as a sheet-like structure, and an embryonic stem cell-derived cell was detached in a state of the single cell. Then, a solution on a dish obtained after the incubation was passed through a cell strainer (filter having a diameter of 70 μm) [manufactured by BD Biosciences], thereby, recovering only an embryonic stem cell-derived cell.

Next, $1 \times 10^6$ cells of the resulting cells were suspended per 100 μL of HBSS solution [manufactured by GIBCO] containing 1% by weight of bovine serum albumin (BSA) [manufactured by SIGMA]. To the resulting cell suspension, anti-VE cadherin antibody and anti-VEGF-R2-antibody were added and then incubated at room temperature for 20 minutes. Thereafter, the resulting product was washed twice with HBSS solution containing 1% by weight of BSA, and subjected to flow cytometry analysis. In the flow cytometry analysis, FACSVantage [manufactured by BD Biosciences] was used.

In addition, alkaline phosphatase activity of a cell obtained by culturing an embryonic stem cell on OP9 cells for 8 days was detected by using HNPP Fluorescent detection kit (manufactured by Roche), and ALP detection kit (manufactured by SIGMA).

As a result, since co-culturing with an OP9 cell was performed in the state where a monkey embryonic stem cell was made into a single cell, a plated monkey embryonic stem cell was evenly differentiated with the passage of time. As shown in Panel A of FIG. 1, expression of VEGFR-2 of which expression was recognized in an undifferentiated embryonic stem cell in flow cytometry analysis was transiently reduced on day 4, and about 8% of cells was again VEGFR-2 positive on day 8.

In addition, as shown in Panel B of FIG. 1, an undifferentiated embryonic stem cell was positive for alkaline phosphatase activity, but as shown in Panel C of FIG. 1, an embryonic stem cell-derived cell population on day 8 was negative for alkaline phosphatase activity which is one of markers of an undifferentiated embryonic stem cell. Therefore, it was thought that the VEGFR-2-positive cell on day 8 was different from a VEGFR-2-positive monkey-derived undifferentiated embryonic stem cell.

Then, the cell on day 8 was subjected to cell sorting by flow cytometry, to sort a VEGFR-2-positive and VE cadherin (which is a marker of a vascular endothelial cell)-negative cell. Conditions upon cell sorting are a cell concentration of $10^6$ cells/ml.

Thereafter, the resulting cell population ($1 \times 10^4$ cells) was plated on an OP9 cell layer of each well of a 24-well dish [manufactured by BD Biosciences], and cultured in a differentiation culture medium for 5 days.

The resulting cell was immunostained with anti-PECAM1 antibody [manufactured by BD Biosciences], anti-VE cadherin antibody [manufactured by BD Biosciences], anti-eNOS antibody [manufactured by BD Biosciences], anti-SMA antibody [manufactured by SIGMA], anti-calponin antibody [manufactured by DAKO] or anti-smooth muscle myosin heavy chain antibody [manufactured by DAKO], as described below.

A culture medium (the differentiation solution) was removed from a culturing container containing cells (including cells in a differentiated form), followed by washing with a phosphate buffered physiological saline (PBS). Then, the cells after washing were fixed by treatment at room temperature for 10 minutes using a 4% by volume paraformaldehyde solution as a fixing solution, when anti-PECAM1 antibody, anti-VE cadherin antibody, anti-eNOS antibody, anti-SMA antibody or anti-calponin antibody was used. In addition, the cells after washing were fixed by treatment at room temperature for 30 minutes using a 70% by volume aqueous ethanol solution as a fixing solution, when anti-smooth muscle myosin heavy chain antibody was used.

Next, the fixing solution was removed, followed by washing with PBS three times. A blocking solution [manufactured by DAKO, blocking reagent; (X0909)] was added to the cells after washing. The resulting product was allowed to stand at room temperature for 1 hour, and thereafter the blocking solution was removed. Then, an anti-PECAM1 antibody solution obtained by 25-fold dilution with an antibody dilution solution [manufactured by DAKO, antibody diluting buffer (S0809)], an anti-VE cadherin antibody solution obtained by 50-fold dilution with the antibody dilution solution, an anti-eNOS antibody solution obtained by 250-fold dilution with the antibody dilution solution, an anti-αSMA antibody solution obtained by 300-fold dilution with the antibody dilution solution, an anti-calponin antibody solution obtained by 75-fold dilution with the antibody dilution solution, or an anti-smooth muscle myosin heavy chain antibody solution obtained by 75-fold dilution with the antibody dilution solution was added to the above cells, and then a primary antibody reaction was performed at room temperature for 1 hour.

After the primary antibody reaction, the resulting product was washed twice with a 0.05M Tris hydrochloric acid buffered physiological saline (TBS: pH 7.6). Thereafter, a labelled secondary antibody [manufactured by DAKO, trade name: ENVISION+Labelled polymer, HRP (K4000) or trade name: Labelled polymer AP (K4017): ready-to-use] was added to the product after washing, and then a secondary antibody reaction was performed at room temperature for 30 minutes.

After the secondary antibody reaction, the solution was removed from the reaction product, the remaining product was washed twice with a 0.05M Tris hydrochloric acid buffered physiological saline (TBS: pH 7.6). The sample after washing was observed.

In addition, double staining for PECAM1 and SMA was performed as follows.

After the culture medium (the differentiation solution) was removed from a culturing container containing cells (including cells in the differentiated state), the cells were washed with a phosphate buffered physiological saline (PBS). The cells were fixed by incubation at room temperature for 30 minutes with a 70% by volume ethanol solution. Staining was carried out by adding an alkaline phosphatase-labelled anti-PECAM1 antibody to the cells after fixation, and thereafter adding BCIP/NBT as a substrate thereto, to thereby cause a color developing reaction.

Then, the resulting product was washed with a 0.05M Tris hydrochloric acid buffered physiological saline (TBS: pH 7.6). Thereafter, staining was carried out by adding a horseradish peroxidase-labelled anti-SMA antibody to the product after washing and thereafter adding DAB as a substrate thereto, to thereby cause a color developing reaction.

The sample after staining was observed under a light field microscope and photographed. The results are shown in FIG. 2.

Figure 2:
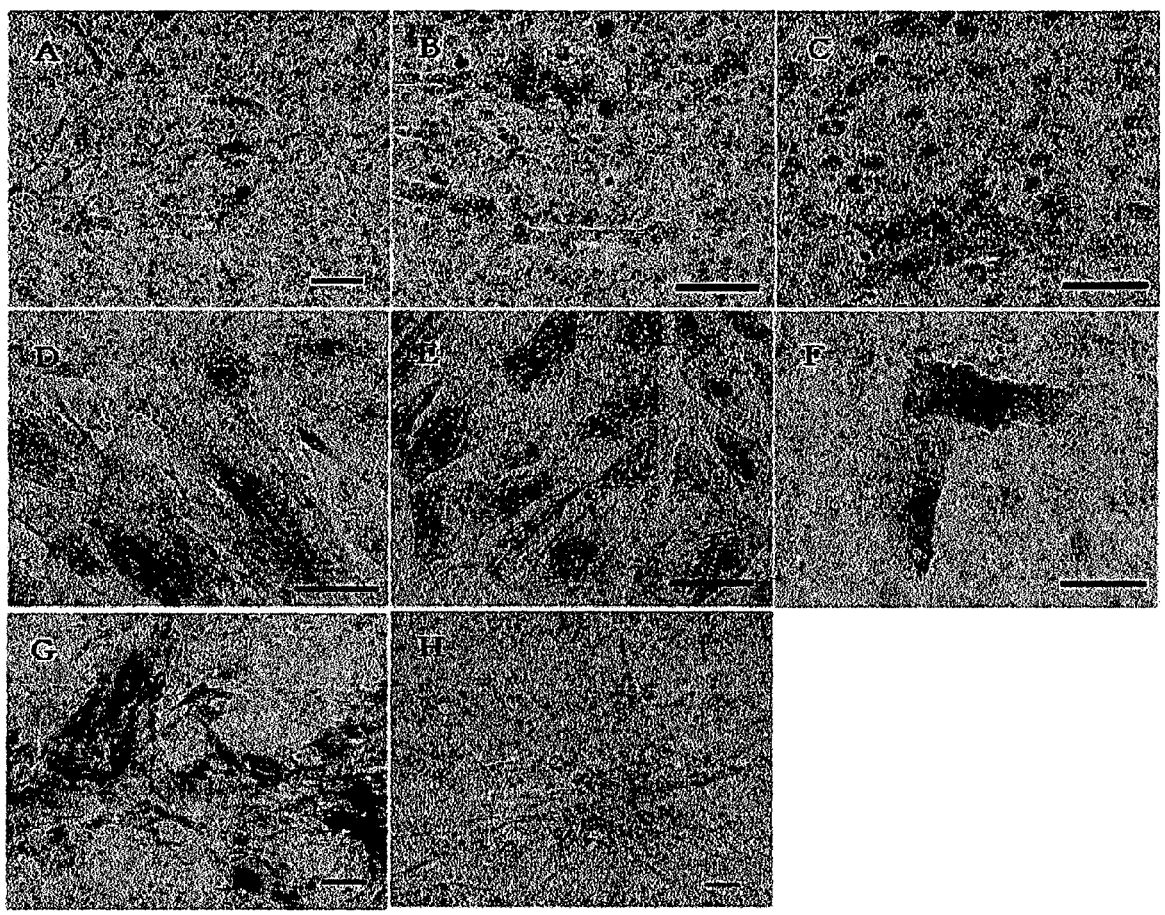
FIG. 2 is a view showing the results of the studies of the properties of cells obtained by the differentiation of a monkey embryonic stem cell. Panels A to C respectively show the results of immunostaining for PECAM1, VE cadherin and eNOS, which are a vascular endothelial cell marker. Panels D to F respectively show the results of immunostaining for smooth muscle actin (αSMA), calponin and smooth muscle myosin heavy chain, which are a mural cell marker. Panel G shows the results of double immunostaining for PECAM1 (brown) and smooth muscle actin (blue). Panel H shows a vascular construct obtained by three-dimensional culture.

As a result, it was found that the VEGFR-2-positive and VE cadherin-negative cell on day 8 from the differentiation was differentiated into a PECAM1-positive, VE cadherin-positive or eNOS-positive vascular endothelial cell as shown in Panel A, Panel B and Panel C of FIG. 2.

In addition, the same VEGFR-2-positive and VE cadherin-negative cells ($2.5 \times 10^3$ cells) were plated on each well of a 96-well dish [manufactured by BD Biosciences] coated with type IV collagen, cultured at 37° C. in 5% by volume of $CO_2$ for 5 days in αMEM culture medium [manufactured by GIBCO] containing 10% by weight of serum. Thereafter, the resulting cells were immunostained in the same manner as described above. Results are shown in FIG. 2.

As a result, it was found that almost all the VEGFR-2-positive and VE cadherin-negative cells were differentiated into an αSMA-positive, calponin-positive or smooth muscle myosin heavy chain-positive mural cell (vascular smooth muscle cell and pericyte) in immunostaining as shown in Panels D, E and F of FIG. 2. The above VEGFR-2-positive and VE cadherin-negative cells were plated on each well of a 96-well dish [manufactured by BD Biosciences] coated with type IV collagen, cultured at 37° C. in 5% by volume of $CO_2$ for 5 days using an αMEM culture medium [manufactured by GIBCO] containing 10% by weight serum and 50 ng/ml of VEGF. The resulting cells were double-stained with anti-α SMA antibody and anti-PECAM1 antibody in the same manner as described above. Results are shown in Panel G of FIG. 2.

As a result, as shown in Panel G of FIG. 2, PECAM1-positive vascular endothelial cells surrounded by αSMA-positive mural cells appeared.

In addition, the VEGFR-2-positive and VE cadherin-negative cells were embedded in a collagen gel (2.0 mg/ml) (trade name: Cellmatrix type 1-A, manufactured by Nitta Gelatin Inc.). The resulting product was placed on a trade name: Cell Disk (manufactured by Sumitomo Bakelite Co., Ltd.). The Cell Disk was placed in a well of a 24-well dish [manufactured by BD Biosciences], and three-dimensionally cultured in a differentiation culture medium [composition: αMEM culture medium containing $5 \times 10^{-5}$M 2-mercaptoethanol and 10% by weight of serum (manufactured by GIBCO)] containing 50 ng/ml of VEGF and 100 pM of phorbol 12-myristate 13-acetate [manufactured by SIGMA]. The results are shown in Panel H of FIG. 2.

As a result, as shown in Panel H of FIG. 2, it was found that a tubular steric vascular structure was constructed.

EXAMPLE 2

Differentiation from Human Embryonic Stem Cell

As a human embryonic stem cell, HES-3 cell strain established in Australia Monash University [Benjamin E. Reubinof et al., *Nature Biotechnology*, 18, 399-404 (2000)] was used.

A human embryonic stem cell was treated at 37° C. for 10 minutes using 0.1% by weight of collagenase (manufactured by Wako Pure Chemical Industries, Ltd.). An undifferentiated human embryonic stem cell was recovered as a small mass by tapping and pipetting. Then, the resulting human embryonic stem cell was plated on an OP9 feeder layer of a gelatin-coated dish in the same manner as in the monkey embryonic stem cell of Example 1.

Regarding the resulting cell, flow cytometry analysis was performed using anti-TRA1-60 antibody [manufactured by Chemicon] and anti-VEGFR-2 antibody in the same manner as in Example 1.

Figure 3:
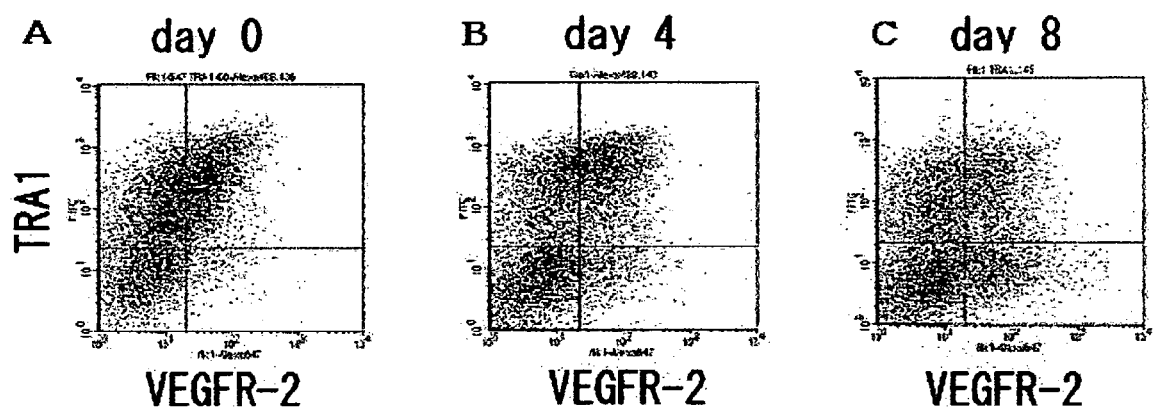
FIG. 3 is a view showing the results of flow cytometry analysis of a human embryonic stem cell and a human embryonic stem cell-derived cell. Panels A to C show expressions of TRA1 and VEGF-R2 in the differentiation on days 0, 4 and 8, respectively.

The human embryonic stem cell as a small mass was co-cultured with the OP9 cells. As shown in FIG. 3, a part of TRA1-60-positive embryonic stem cells remained undifferentiated during the process of the differentiation by co-culturing.

In addition, as shown in Panel C of FIG. 3, about 15% of a VEGFR-2-positive and TRA1-60-negative cell population which is different from an undifferentiated embryonic stem cell appeared on day 8.

The cell which appeared on day 8 was subjected to cell sorting by flow cytometry, to sort VEGFR-2-positive and TRA1-60-negative cells. The conditions for cell sorting are a cell concentration of $10^6$ cells/ml.

The resulting cells were plated on a 96-well dish [manufactured by BD Biosciences] coated with type IV collagen, and cultured at 37° C. in 5% by volume of $CO_2$ for 8 days using αMEM culture medium [manufactured by GIBCO] containing 10% by weight of serum, in the same manner as that of Example 1.

Then, regarding the resulting cell, immunostaining was performed using anti-αSMA antibody [manufactured by BD Biosciences] or anti-calponin antibody [manufactured by DAKO] in the same manner as in Example 1.

Figure 4:
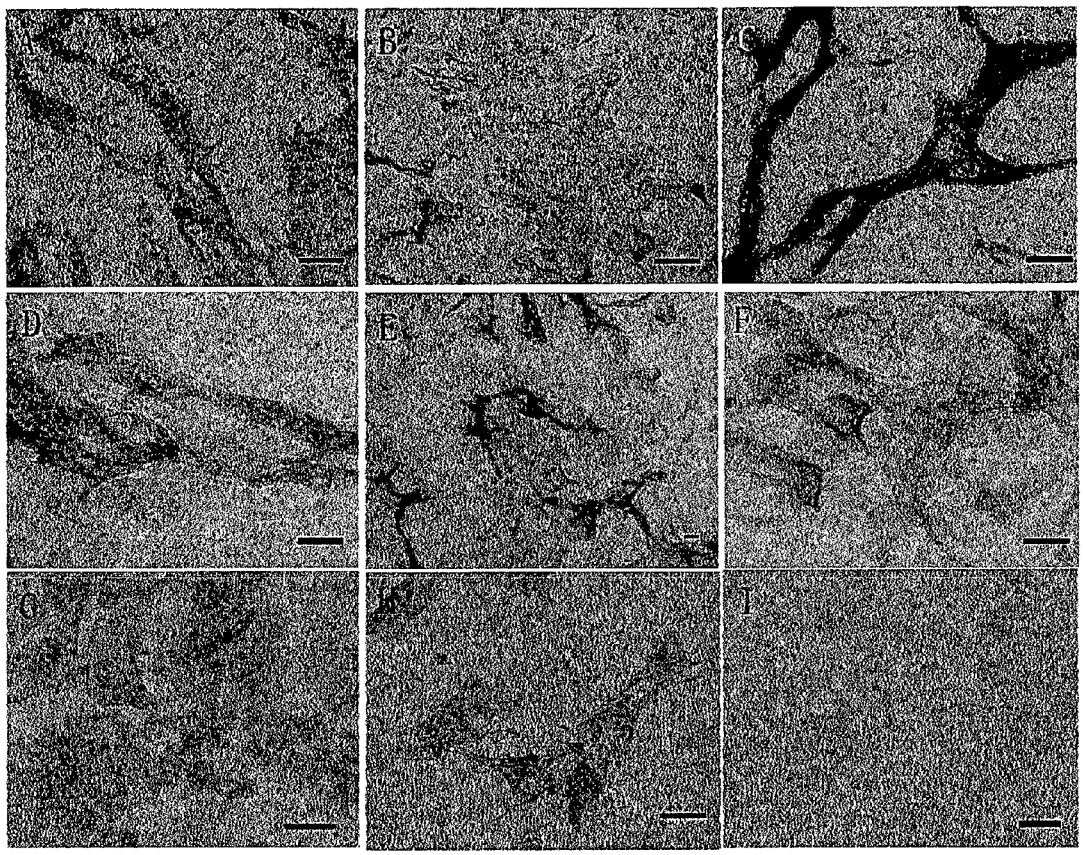
FIG. 4 is a view showing the results of immunohistochemical analysis of the differentiation of a human embryonic stem cell into a vascular cell. Panels A to D are the results of immunostaining for an endothelial cell marker. Panel A shows immunostaining for CD34, Panel B being immunostaining for VE cadherin, Panel C being immunostaining for PECAM1, and Panel D being immunostaining for eNOS. Panel E shows double immunostaining for PECAM1 (blue) and smooth muscle actin (brown). Panels F to H are the results of immunostaining for a mural cell marker. Panel F shows immunostaining for αSMA, Panel G being immunostaining for calponin, and Panel H being immunostaining for αSMA. Panel I shows a vascular construct obtained by three-dimensional culture. Each scale bar indicates 50 μm.

As a result, as shown in each of Panels F and G of FIG. 4, it was found that almost all the cells were differentiated into αSMA-positive or calponin-positive mural cells.

In addition, when the VEGFR-2-positive and TRA1-60-negative cells were cultured at 37° C. in 5% by volume of $CO_2$ using αMEM culture medium [manufactured by GIBCO] containing 10 ng/ml of PDGF-BB [manufactured by Peprotech] in place of 10% by weight of serum, almost all cells were differentiated into mural cells as shown in Panel H of FIG. 4.

Differentiation was performed at 37° C. in 5% by volume of $CO_2$ for 8 days on the same 96-well dish coated with type IV collagen using a culture medium obtained by adding 50 ng/ml of VEGF to αMEM culture medium [manufactured by GIBCO] containing 10% by weight of serum. The resulting cell was immunostained with anti-CD34 antibody [manufactured by DAKO], anti-PECAM1 antibody [manufactured by BD Biosciences], anti-VE cadherin antibody [manufactured by BD Biosciences], anti-eNOS antibody [manufactured by BD Biosciences], anti-SMA antibody [manufactured by SIGMA] or anti-calponin antibody [manufactured by DAKO] in the same manner as described above. When anti-PECAM1 antibody was used, the cells after washing were fixed by treatment at room temperature for 10 minutes using a 4% by volume paraformaldehyde solution as a fixing solution.

As a result, as shown in Panels A, B, C and D of FIG. 4, CD34-positive, VE cadherin-positive, PECAM1-positive or eNOS-positive vascular endothelial cells appeared.

In addition, as shown in Panel E of FIG. 4, cells other than a vascular endothelial cell were differentiated into αSAM-positive mural cells.

In addition, these VEGFR-2-positive and TRA1-60-negative cells were embedded in a collagen gel (2.0 mg/ml) (trade name: Cellmatrix type 1-A, manufactured by Nitta Gelatin Inc.). The resulting product was placed on a trade name: Cell Disk (manufactured by Sumitomo Bakelite Co., Ltd.), and then the Cell Disk was placed in a well of a 24-well dish [manufactured by BD Biosciences]. The cells were three-dimensionally cultured in a differentiation culture medium [composition: αMEM culture medium (manufactured by GIBCO) containing $5 \times 10^{-5}$M 2-mercaptoethanol and 10% by weight of serum] containing 50 ng/ml of VEGF and 100 pM of phorbol 12-myristate 13-acetate [manufactured by SIGMA]. As a result, as shown in Panel I, it was found that a tubular steric vascular structure was constructed.

COMPARATIVE EXAMPLE

A VEGFR-2-positive cell was differentiated from each of a monkey ES cell and a human ES cell in the same conditions as in the differentiation from a mouse ES cell into a VEGFR-2-positive cell.

As a result, in the case of a monkey ES cell and a human ES cell, the cell was not grafted well on collagen IV, unlike a mouse ES cell.

In addition, upon the differentiation of a mouse ES cell, the differentiation can be achieved by using cells as a single cell, but in the case of a human ES cell, almost all the cells died when cells were used as a single cell.

On the other hand, when in a human and a monkey, a vascular endothelial cell or a mural cell was differentiated from a VEGFR-2-positive cell according to the methods of Examples 1 and 2, about 2-fold days were required as compared with the case of a mouse.

Further, the differences in viabilities between a mouse vascular progenitor cell and a human vascular progenitor cell (VPC) are shown in Table 1.

TABLE 1

| | Viability of Cell | Proliferation Rate |
| --- | --- | --- |
| Mouse | Cells die in a week or so under in vitro conditions. | The rate cannot be determined, since cells die in a week or so. |
| Human | Cells are viable for a long term (confirmed survival being about one month) under in vitro conditions. | Cells are proliferated twice, for about four days (96 hours). |

From the above results, in the same differentiation method as the case of a mouse, it is found that it is difficult to differentiate a VEGFR-2-positive cell from each of a monkey ES cell and a human ES cell.

EQUIVALENTS

The invention may be embodied in other various forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. An in vitro method for differentiating a primate embryonic stem cell selected from CMK-6 cell strain or HES-3 cell strain into a vascular cell selected from the group consisting of a vascular endothelial cell, a mural cell and a vascular construct, comprising differentiating a primate embryonic stem cell into a vascular endothelial growth factor receptor (VEGFR-2)-positive cell, wherein the differentiated vascular cell lacks at least one of ALP, SSEA-3, SSEA-4, TRA1-60 and TRA1-81, wherein said differentiating comprises the steps of:
   (I) co-culturing a primate embryonic stem cell with a feeder cell which includes OP9 cell strain, to differentiate into a cell population A comprising said vascular endothelial growth factor receptor (VEGFR-2)-positive and undifferentiated primate stem cell marker-negative cell, and
   (II) separating substantially said VBGFR-2-positive and undifferentiated primate embryonic stem cell marker-negative cell from the cell population A obtained in the above step (I).

2. The differentiation method according to claim 1, wherein said vascular cell is a vascular progenitor cell.

3. A differentiation method according to claim 1, comprising differentiating a cell culture comprising a plurality of said primate embryonic stem cells into a culture comprising a plurality of said vascular cells.

4. The method according to claim 1, wherein said vascular cell is an endothelial cell.

5. The method according to claim 1, wherein said vascular cell is a mural cell.

6. The method according to claim 1, wherein said vascular cell is a vascular construct.

7. The differentiation method according to claim 5, further comprising the steps of:
   (III) culturing said VBGFR-2-positive and undifferentiated primate embryonic stem cell marker-negative cell obtained in said step (II) in the presence of serum or PDGF-BB, to differentiate into a cell population B comprising a mural cell marker-positive cell, wherein the mural cell marker is selected from α smooth muscle actin (α SMA) or calponin, and (IV) separating substantially said mural cell marker- positive cell from the cell population B obtained in said step (III).

8. The differentiation method according to claim 4, further comprising the steps of:
   (III') culturing said VEGFR-2-positive and undifferentiated primate embryonic stem cell marker-negative cell obtained in said step (II) in the presence of VEGF, to differentiate into a cell population C comprising a vascular endothelial cell marker-positive cell, wherein the vascular endothelial cell marker is selected from the group consisting of CD34, VE cadherin, PECAM1 and eNOS, and
   (IV') separating substantially said vascular endothelial cell marker-positive cell from the cell population C obtained in said step (III').

9. The differentiation method according to claim 6, comprising the steps of:
   (III") culturing three-dimensionally said VEGFR-2-positive and undifferentiated primate embryonic stem cell marker-negative cell obtained in said step (II) in the presence of VEGF and phorbol 12-myristate 13-acetate within a carrier.

10. An in vitro method for producing a vascular mural cell, comprising the steps of:
    (I) co-culturing a primate embryonic stem cell selected from CMK-6 cell strain or HES-3 cell strain with a feeder cell which includes OP9 cell strain, to differentiate into a cell population A comprising a vascular endothelial growth factor receptor (VEGFR-2)-positive and undifferentiated primate embryonic stem cell marker-negative cell, wherein the differentiated vascular cell lacks at least one of ALP, SSEA-3, SSEA-4, TRA1-60 and TRA1-81,
    (II) separating substantially said VEGFR-2-positive and undifferentiated primate embryonic stem cell marker-negative cell from the cell population A obtained in the above step (I),
    (III) culturing said VEGFR-2-positive and undifferentiated primate embryonic stem cell marker-negative cell obtained in the above step (II) in the presence of serum or PDGF-BB, to differentiate into a cell population B comprising a mural cell marker-positive cell, wherein the mural cell marker is selected from a smooth muscle actin (α SMA) or calponin, and
    (IV) separating substantially said mural cell marker-positive cell from the cell population B obtained in the above step (III).

11. An in vitro method for producing a vascular endothelial cell, comprising the steps of
    (I) co-culturing a primate embryonic stem cell selected from CMK-6 cell strain or HES-3 cell strain with a feeder cell which includes OP9 cell strain, to differentiate into a cell population A comprising a vascular endothelial growth factor receptor (VEGFR-2)-positive and undifferentiated primate embryonic stem cell marker-negative cell, wherein the differentiated vascular cell lacks at least one of ALP, SSEA-3, SSEA-4, TRA1-60 and TRA1-8,
    (II) separating substantially said VEGFR-2-positive and undifferentiated primate embryonic stem cell marker-negative cell from the cell population A obtained in the above step (I),
    (III') culturing said VEGFR-2-positive and undifferentiated primate embryonic stem cell marker-negative cell obtained in the above step (II) in the presence of VEGF, to differentiate into a cell population C comprising a vascular endothelial cell marker-positive cell, wherein the vascular endothelial cell marker is selected from the group consisting of CD34, VE cadherin, PECAM1 and eNOS, and
    (IV') separating substantially said vascular endothelial cell marker-positive cell from the cell population C obtained in the above step (III').

12. An in vitro method for producing a vascular construct cell, comprising the steps of:
    (I) co-culturing a primate embryonic stem cell selected from CMK-6 cell strain or HES-3 cell strain with a feeder cell which includes OP9 cell strain, to differentiate into a cell population A comprising a vascular endothelial growth factor receptor (VEGFR-2)-positive and undifferentiated primate embryonic stem cell marker-negative cell, wherein the differentiated vascular cell lacks at least one of ALP, SSEA-3, SSEA-4, TRA1-60 and TRA1-81,
    (II) separating substantially said VEGFR-2-positive and undifferentiated primate embryonic stem cell marker-negative cell from the cell population A obtained in the above step (I), and
    (III") culturing three-dimensionally said VEGFR-2-positive and undifferentiated primate embryonic stem cell marker-negative cell obtained in the above step (II) in the presence of VEGF and phorbol 12-myristate 13-acetate within a carrier.

* * * * *